(12) United States Patent
Fischer, Sr.

(10) Patent No.: US 6,269,272 B1
(45) Date of Patent: Jul. 31, 2001

(54) CARDIAC PACEMAKER LEAD WITH DUAL PITCH FIXATION APPARATUS

(75) Inventor: Elmar R. Fischer, Sr., Lake Jackson, TX (US)

(73) Assignee: Intermedics, Inc., Angleton, TX (US)

(*) Notice: Subject to any disclaimer, the term of this patent is extended or adjusted under 35 U.S.C. 154(b) by 0 days.

(21) Appl. No.: 09/366,401

(22) Filed: Aug. 3, 1999

(51) Int. Cl.⁷ .................................................. A61N 1/05
(52) U.S. Cl. ........................................................ 607/127
(58) Field of Search .................................. 607/122, 126, 607/127, 128

(56) References Cited

U.S. PATENT DOCUMENTS

| | | | |
|---|---|---|---|
| 4,106,512 | 8/1978 | Bisping | 128/418 |
| 4,233,992 | 11/1980 | Bisping | 128/785 |
| 4,538,623 | 9/1985 | Proctor et al. | 128/784 |
| 5,246,014 | 9/1993 | Williams et al. | 607/122 |
| 5,282,845 | 2/1994 | Bush et al. | 607/128 |
| 5,300,108 | 4/1994 | Rebell et al. | 607/127 |
| 5,324,327 | 6/1994 | Cohen | 607/122 |
| 5,385,579 | 1/1995 | Helland | 607/130 |
| 5,514,173 | 5/1996 | Rebell et al. | 607/127 |
| 5,593,433 | 1/1997 | Spehr et al. | 607/128 |
| 5,697,804 | 12/1997 | Froberg et al. | 439/346 |
| 5,769,858 | 6/1998 | Pearson et al. | 606/108 |
| 5,840,031 | 11/1998 | Crowley | 600/440 |
| 5,851,226 | 12/1998 | Skubitz et al. | 607/126 |
| 5,897,584 | 4/1999 | Herman | 607/122 |

*Primary Examiner*—Scott M. Getzow
(74) *Attorney, Agent, or Firm*—Schwegman, Lundberg, Woessner & Kluth, P.A.

(57) ABSTRACT

A cardiac stimulator lead is provided that includes a connector for connecting to a cardiac stimulator and a tubular insulating sleeve that has a first end coupled to the connector and a second end. An electrode is coupled to the second end and has a longitudinal bore. An extendable/retractable corkscrew is positioned in the bore. The cork screw has a selected pitch and is mounted on a threaded shaft. Threads on the shaft have a different pitch from the pitch of the cork screw, preferably a pitch less than that of the cork screw, and most preferably a pitch about half that of the corkscrew.

34 Claims, 4 Drawing Sheets

CARDIAC PACEMAKER LEAD WITH DUAL PITCH FIXATION APPARATUS

FIELD OF THE INVENTION

This invention relates generally to cardiac stimulator leads, and more particularly to a cardiac stimulator lead having an extendable and retractable screw-in fixation mechanism.

DESCRIPTION OF THE RELATED ART

Conventional cardiac stimulator systems consist of a cardiac stimulator and at least one elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines. The proximal end of the lead is then connected to the cardiac stimulator and the incision is closed. The implantation route and site are usually imaged in real time by fluoroscopy to confirm proper manipulation and placement of the lead.

A conventional cardiac stimulator lead normally consists of an elongated, flexible, tubular, electrically insulating sleeve that is connected proximally to a connector that is adapted to couple to the header of a cardiac stimulator, and distally to a tubular tip electrode. One or more ring-type electrodes may be secured to the sleeve at various positions along the length of the sleeve. The proximal end of the lead sleeve is connected to the connector by application of various biocompatible adhesives to various portions of the connector and the sleeve. The tip electrode ordinarily consists of a tubular structure that has an increased diameter portion that forms an annular shoulder against which the distal end of the lead sleeve abuts. The exterior surface of the tubular structure is normally smooth, as is the interior surface of the distal end of the lead sleeve.

In conventional active fixation tip electrodes, engagement with the endocardium is often achieved by projecting a corkscrew from the electrode. This is normally carried out by twisting the corkscrew. As the corkscrew spirals outward from the tip, the piercing point of the corkscrew pierces the endocardium, enabling the corkscrew to be screwed into the tissue by further twisting. The axial movement of the corkscrew relative to the tip electrode is usually accomplished by providing the electrode with a set of internal threads cut to match the pitch of the coils of the corkscrew. A stylet is inserted into the lead and temporarily coupled to the corkscrew. The stylet is twisted by hand to rotate the corkscrew.

The most common method of verifying a proper engagement of the endocardium by the corkscrew is by touch. Following deployment of the corkscrew, the physician applies a gentle, axial, tensile force on the lead connector. An absence of appreciable longitudinal movement of the lead is an indication that the corkscrew has successfully penetrated and engaged the tissue. However, a sudden longitudinal movement of the lead is an indication that the corkscrew either did not engage enough tissue or did not engage any tissue at all. In such circumstances, the physician must retract the corkscrew, reposition the tip of the lead proximate the targeted tissue, and redeploy the corkscrew. This process may be very time consuming, particularly where very precise electrode positioning is medically indicated and the targeted tissue is difficult to reach, e.g. requires complex bending and manipulation of the stylet. The problem of tissue engagement verification may be aggravated by other aspects of conventional tip electrode and corkscrew design. In most conventional leads, the corkscrew is deployed by a set of internal threads in the tip electrode. The threads extend from some point within the electrode to the opening at the distal end of the electrode from which the corkscrew deploys. A by-product of this design is that the corkscrew deploys as soon as the stylet is twisted. This may not be problematic where the tip is positioned and maintained in close contact with the targeted tissue. However, if the tip is not bearing directly against the targeted tissue or not positioned within a fraction of the total length of the corkscrew at the time the stylet is twisted, the corkscrew may deploy and either not engage any tissue at all or only penetrate a small distance into the tissue. In the former situation, the corkscrew will have to be retracted and second attempt made. In the latter scenario, two undesirable outcomes may result. First, a less than optimum amount of tissue penetration may result. Second, minimal tissue penetration by a fully extended corkscrew may result in the conducting tip of the electrode having only intermittent physical contact with the targeted tissue or no contact at all.

The present invention is directed to overcoming or reducing the effects of one or more of the foregoing disadvantages.

SUMMARY OF THE INVENTION

In accordance with one aspect of the present invention, a cardiac stimulator lead is provided. The lead includes a connector for connecting to a cardiac stimulator and a tubular insulating sleeve that has a first end coupled to the connector and a second end. An electrode is coupled to the second end and has a longitudinal bore. A washer is disposed in the bore for restricting the influx of body fluids into the sleeve. A conductor wire is disposed in the sleeve and coupled between the connector and the electrode for transmitting electric signals between the cardiac stimulator and the electrode.

A corkscrew is coupled to the electrode and is extendable from and retractable into the bore. The lead includes means for transmitting torque from the pin member to the corkscrew. The cork screw has a selected pitch and is mounted on a threaded shaft. Threads on the shaft have a different pitch from the pitch of the cork screw, preferably a pitch less than that of the cork screw, and most preferably a pitch about half that of the corkscrew. When the corkscrew is advanced out of the lead, it engages the cardiac wall. Because of the larger pitch of the corkscrew, the corkscrew drives into the heart wall faster than the corkscrew is exposed outside the tip of the lead. This pulls the lead tip securely against the heart wall. If the tip is also an electrode, a better electrical connection is made between the electrode and the heart.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
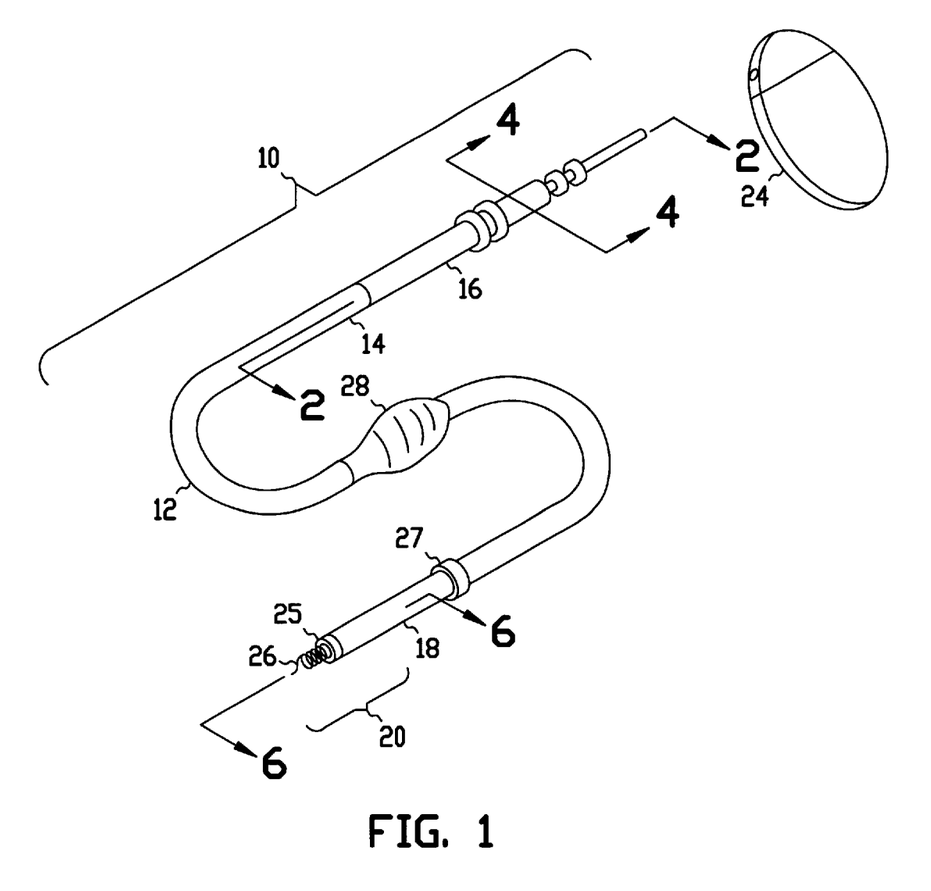
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac stimulator lead 10 that includes a flexible insulating sleeve 12 that has a proximal end 14 coupled to a connector 16, and a distal end 18 coupled to a tip electrode 20. The connector 16 is designed to be inserted into a cardiac stimulator 24, and is shown highly exaggerated in size relative to the cardiac stimulator 24. The cardiac stimulator 24 may be a pacemaker, a cardioverter/defibrillator, or other type of stimulator or a sensing instrument. The tip electrode 20 includes a tip 25 and a corkscrew 26 projectable therefrom to engage and actively secure the lead 10 to myocardial tissue. The illustrated embodiment of the lead 10 is bipolar. Accordingly, the distal end 18 is provided with an electrode 27 located proximal to the tip electrode 20. However, unipolar or other multi-polar arrangements are possible as well. A suture sleeve 28 is slipped over the sleeve 12. During implantation, the suture sleeve 28 is sewn to body tissue at the site of transvenous entry.

The sleeve 12 is a flexible tubular member that provides a robust, electrically insulating coupling between the connector 16 and the electrode 20. The sleeve 12 protects one or more fine gage conductor wires enclosed therein from body fluids and tissues, and is advantageously composed of a biocompatible, electrically insulating material, such as silicone, polyurethane, or like materials.

Figure 2:
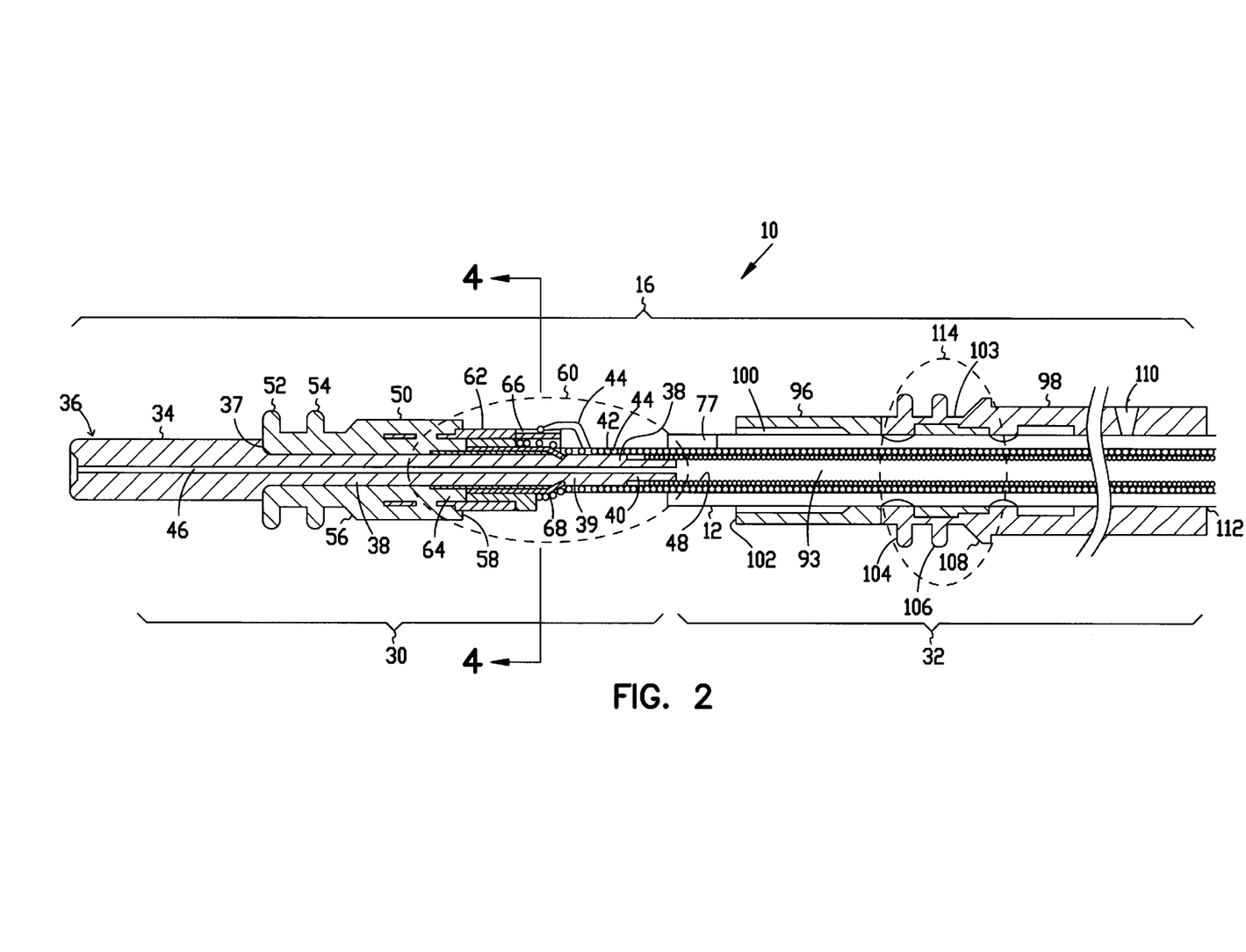
FIG. 2 is a cross-sectional view of the cardiac lead of FIG. 1 taken at section 2—2 in accordance with the present invention.

The detailed structure of the connector 16 may be understood by referring now to FIG. 2, which is a cross-sectional view of FIG. 1 taken at section 2—2. The connector 16 includes a connector pin assembly 30 coupled to a connector sleeve assembly 32. For clarity of illustration, the connector pin assembly 30 and the connector sleeve assembly 32 are shown exploded. The connector pin assembly 30 includes a tubular pin member 34 that has an elongated proximal end 36 designed to make electrical contact with one or more electrical contacts inside the cardiac stimulator 24 depicted in FIG. 1, and serves as a handle for twisting the pin 34 to manipulate the corkscrew 26 as described below. The distal end of the pin 34 consists of an intermediate shank 38 that tapers down from the proximal end 36 to establish an annular shoulder 37, an intermediate shank 39, and a distal shank 40. The intermediate shank 39 is suitably sized to accommodate the nested coils of a conductor wire 42 and another conductor wire 44. The distal shank 40 is sized to receive the coils of a torque coil 48. The wire 42 is electrically connected distally to the tip electrode 20 depicted in FIG. 1, and the wire 44 is electrically connected distally to the annular electrode 27 depicted in FIG. 1. The connections of the wires 42 and 44 to the pin assembly 30 will be described in more detail below. A lumen 46 extends through the pin member 34.

A first insulating sleeve 50 is coupled to the exterior of the pin member 34. The first insulating sleeve 50 includes longitudinally spaced-apart O-rings 52 and 54 that are designed to engage structures within the cardiac stimulator 24 shown in FIG. 1 and to provide a seal for the pin member 34 against the intrusion of body fluids following implantation. A single O-ring may be used in place of the pair 52 and 54. The first insulating sleeve 50 is provided with a proximally facing chamfer surface 56 that is principally designed to provide a tapered surface to facilitate easy insertion of the connector 16 into the cardiac stimulator 24 shown in FIG. 1. The distal end of the first insulating sleeve 50 includes a distally facing annular surface 58 against which the conductor sleeve assembly 32 is abutted when the connector 16 is assembled. The first insulating sleeve 50 is advantageously composed of a biocompatible flexible material that may be advantageously injection molded around the pin member 34. The material may be silicone, polyurethane, or like materials. In this way, the O-rings 52 and 54 may be formed integrally with the first insulating sleeve 50. Alternatively, the first insulating sleeve 50 may be provided with external grooves and the O-rings 52 and 54 secured to the first insulating sleeve 50 as separate members.

Figure 3:
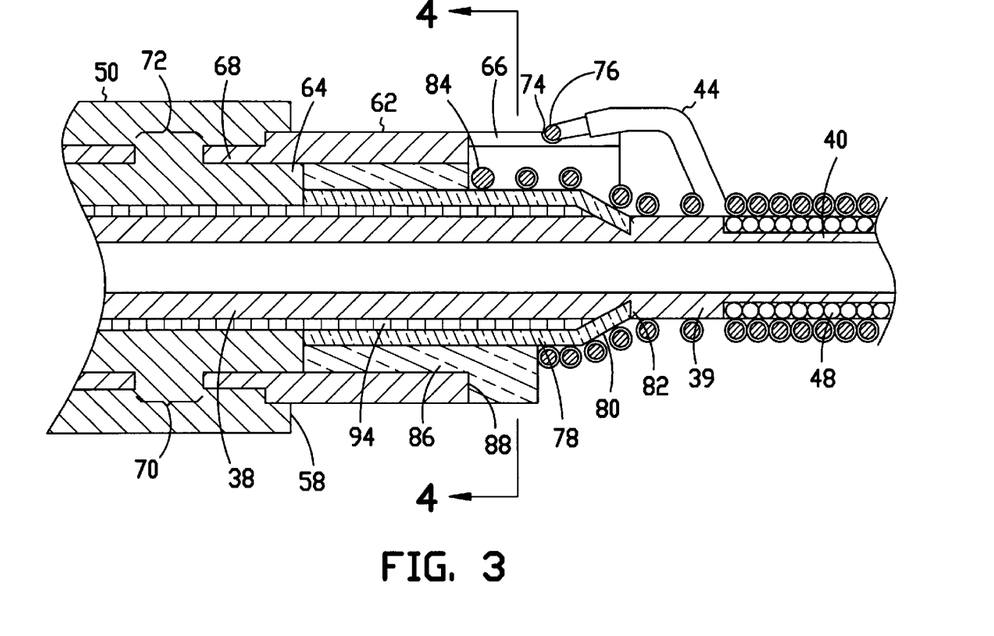
FIG. 3 is a close-in view of a portion of the lead shown in FIG. 2.
Figure 4:
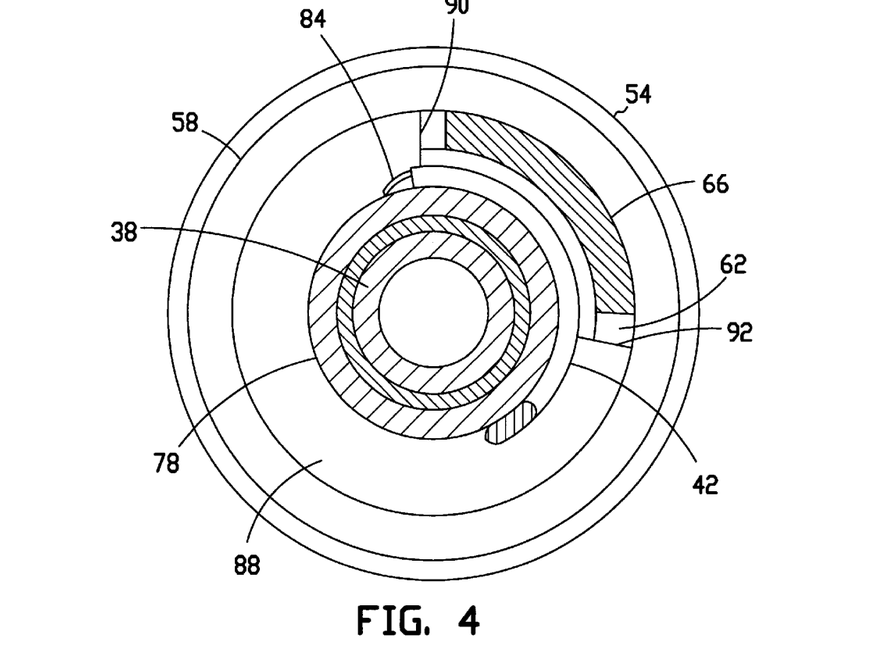
FIG. 4 is a cross-sectional view of FIGS. 2 and 3 taken at section 4—4 in accordance with the present invention.

Referring now also to FIG. 3, which is a detailed view of the portion of FIG. 2 circumscribed by the dashed oval 60, and to FIG. 4, which is a cross-sectional view of FIG. 3 taken at section 4—4, an annular member 62 is disposed around a reduced diameter portion 64 of the sleeve 50. The annular member 62 includes a distally projecting flag 66 to which the conductor wire 44 is attached and which provides an electrical pathway between the wire 44 and a contact (not shown) within the cardiac stimulator 24 shown in FIG. 1. The annular member 62 includes a proximally projecting reduced diameter nipple 68 that projects into the first insulating sleeve 50. The nipple has two or more circumferentially spaced ports 70 and 72 that enable molded structure to harden therein and provide a secure mechanical engagement between the first insulating sleeve 50 and the annular member 62. The flag 66 is provided with an external circumferential groove 74 that is dimensioned to receive the stripped end 76 of the conductor wire 44. The stripped end 76 is secured to the flag 66 by laser welding or like welding techniques.

As best seen in FIG. 2, the sleeve 12 is provided with a longitudinally extending slot 77 that is slightly wider than the outer diameter of the wire 44. The slot 77 provides a space to accommodate the wire 44 so that the sleeve 12 may be pushed past the wire 44 and abutted against the reduced diameter portion 64.

Electrical connection between the conductor wire 42 and the pin member 34 is established by a cylindrical contact sleeve 78 through which the pin member 34 is journalled and which is disposed partially within the annular member 62. The contact sleeve 78 abuts proximally against the reduced diameter portion 64 and is provided distally with an inwardly tapering portion 80 that engages a notch in the pin member 34 at 82. The engagement between the tapered portion 80 and the notch 82 serves to retain the pin member 34 within the connector pin assembly 30. As discussed more below, the pin member 34 is rotated to extend and/or retract the corkscrew 26 depicted in FIG. 1. The skilled artisan will appreciate that if the conductor wire 42 is allowed to rotate with the pin member 34, the wire 42 may become damaged or provide undesirable resistance to the rotation of the pin member 34. Accordingly, the fit provided between the tapered portion 80 and the notch 82 is such that the pin member 34 may readily be rotated relative to the fixed contact sleeve 78 while still maintaining sufficient contact between the pin member 34 and the contact sleeve 80 such that electrical conductivity between the conductor wire 42 and the pin member 34 is retained. As best seen in FIG. 4, the wire 42 is stripped at 84 and secured to the contact sleeve 78 by laser welding or like techniques. Electrical isolation between the annular member 62 and the contact sleeve 78 is provided by an annular bushing 86 that includes distally disposed annular flange 88 shoulders against the distal end of the annular member 62. The flange is not coextensive with the entire circumference of the bushing 86. Instead, the flange 78 includes a cutout, best seen in FIG. 4, extending from the surface 90 to the surface 92. The cutout is provided to accommodate the flag 66.

The embodiment depicted in FIGS. 1, 2, 3, and 4, is bipolar. However, a unipolar arrangement may be implemented by incorporating a single conductor wire, such as the wire 42, that is coupled to either the pin member 34 or to the flag 66. Similarly, the conductor wires 42 and 44 are depicted as single individually insulated wires with insulation stripped prior to welding to contact sleeve 68 and the flag 66. However, the skilled artisan will appreciate that the conductor wires 42 and 44 may not be individually insulated if the lead 10 is unipolar or if the various conductor wires in the lead 10 are coaxially arranged or arranged in a nested configuration.

Referring again specifically to FIGS. 2 and 3, the torque coil 48 is secured to the distal shank 40 by laser welding or like welding techniques. The pitch of the individual coils in the torque coil 48 is largely a matter of design discretion. The skilled artisan will appreciate that as the pitch of the coils is increased, the torque carrying capabilities of the coil 48 will decrease unless the stiffness of the material used to fabricate the coil 48 is proportionally increased. The torque coil 48 is advantageously composed of a biocompatible material with sufficient stiffness to readily transmit torque from the pin member 34 to the corkscrew 26 depicted in FIG. 1. Exemplary materials include MP35N alloy, 316L stainless steel, or like materials. The torque coil 48 and the wires 42 and 44 extend longitudinally through the lumen 93 of the sleeve 12 to the tip electrode 20.

It is desirable to electrically isolate the annular member 62 from the pin member 34 to alleviate the potential for short circuiting. This is particularly important during electrical verification testing, which is normally done at relatively high voltage. The primary electrical insulation is provided by the first insulating sleeve 50, and particularly the reduced diameter portion 64, as well as the bushing 86. It is anticipated that the material used to fabricate the first insulating sleeve 50 will readily fill the space, and provide a complete electrically insulating separation between the annular member 62 and the pin member 34. However, the skilled artisan will appreciate that there is the possibility of void formation during the molding process due to air bubbles or other mechanisms. If a void is formed in the reduced diameter portion 64 between the annular member 62 and the pin member 34, destructive arcing may occur in the void during high voltage electrical verification testing of the lead 10. To reduce the possibility of shorts through a void formed in the reduced diameter portion 64, an insulating annular member 94 may be slipped over the intermediate shank 38 and abutted proximally against the shoulder 37 prior to molding of the first insulating sleeve 50. The insulating annular member 94 may be composed of a variety of biocompatible insulating materials such as, for example, polyimide, polyurethane, or like materials.

Referring again to FIG. 2, the connector sleeve assembly 32 includes a conductor sleeve 96 that is coupled to a second insulating sleeve 98. The second insulating sleeve 98 is a tubular member of such length and the scale of FIG. 2 is such that the second insulating sleeve 98 is shown broken. The conductor sleeve 96 includes a proximally disposed bore 100 that is dimensioned so that the conductor sleeve 96 may be readily slipped over the annular member 62 until the annular surface 102 of the conductor sleeve 96 abuts the annular shoulder 58 of the first insulating sleeve 50. The conductor sleeve 96 is designed to establish an electrical pathway between the annular member 62 and a conducting structure inside the cardiac stimulator 24 shown in FIG. 1. Accordingly, the fit between the internal diameter of the conductor sleeve 96 and the outer diameter of the annular member 62 should be close enough to provide good electrical contact. The conductor sleeve 96 is coupled to the annular member 62 by laser welding or like techniques.

The proximal end 103 of the second insulating sleeve 98 is provided with two longitudinally spaced-apart O-rings 104 and 106 that serve to seal the conductor sleeve 96 against the intrusion of body fluids after the lead 10 is coupled to the cardiac stimulator 24 shown in FIG. 1. As with the aforementioned O-rings 52 and 54, the O-rings 104 and 106 may be integrally molded into the second insulating sleeve 98 or attached as separate members. On the distal side of the O-ring 106, the second insulating sleeve 98 expands in diameter and defines a chamfer surface 108 that provides the same functionality as the chamfer surface 56, albeit in conjunction with a different portion of the internal structure of the cardiac stimulator 24 shown in FIG. 1. The internal diameter of the second insulating sleeve 98 is generally dimensioned to provide a sliding fit with the outer surface of the sleeve 12 to permit easy assembly. The second insulating sleeve 98 is secured to the sleeve 12 by a suitable biocompatible medical grade adhesive, such as silicone, or any of a variety of two stage adhesives. To facilitate the introduction and spreading of the adhesive, the second insulating sleeve 98 is provided with a port 110. Adhesive is introduced into the port 110 under slight pressure to encourage the rapid and uniform spreading of the adhesive around the sleeve 12. The flow characteristics of the adhesive may be enhanced by thinning with a suitable diluent, such as heptane, prior to injection through the port 110. In addition, adhesive is back filled between the second insulating sleeve 98 and the sleeve 12 by injection under slight pressure at the interface designated 112.

Figure 5:
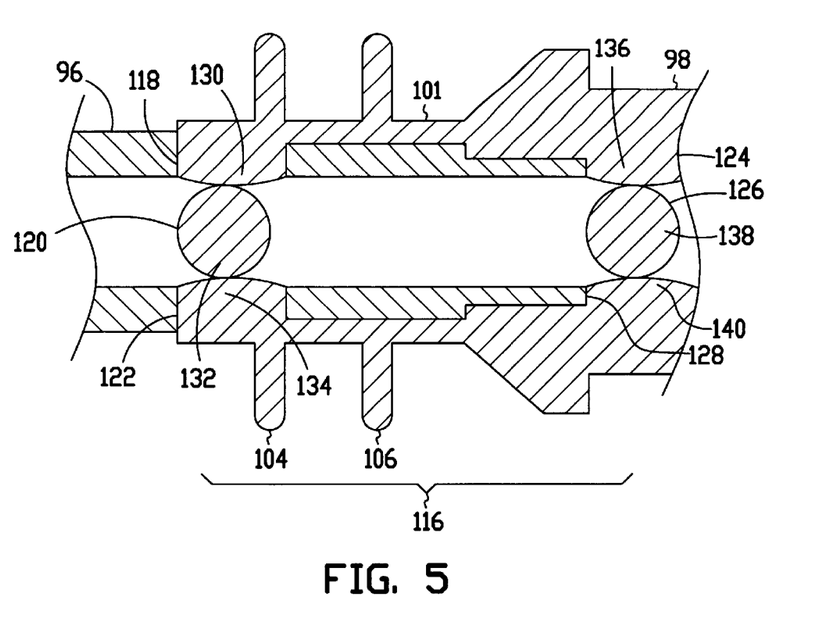
FIG. 5 is a close-in view of a portion of the lead shown in FIG. 2 depicting another portion of the connector in accordance with the present invention.

The connection between the conductor sleeve 96 and the second insulating sleeve 98 may be more readily understood by referring now to FIG. 5, which is a magnified view of the portion of FIG. 2 circumscribed by the dashed oval 114. Note that in FIG. 5, the sleeve 12 is not shown for clarity of illustration. A central portion 116 of the conductor sleeve 96 is provided with a plurality of circumferentially spaced bores, six of which are depicted at 118, 120, 122, 124, 126, and 128. The bores 118, 120, 122, 124, 126, and 128 are designed to enable the material used to mold the second insulating sleeve 98 to flow into the bores 118, 129, 122, 124, 126, and 128 and harden into buttons 130, 132, 134, 136, 138, and 140. The engagement between the buttons 130, 132, 134, 136, 138, and 140 and the central portion 116 of the conductor sleeve 96 establishes a secure mechanical engagement between the conductor sleeve 96 and the second insulating sleeve 98. The second insulating sleeve 98 is advantageously composed of the same types of materials used to fabricate the first insulating sleeve 50 shown in FIG. 2, and is advantageously injection molded.

The pin member 34, the annular member 62, and the conductor sleeve 96 are advantageously composed of a biocompatible conducting material that may be welded via laser or like techniques. Exemplary materials include 316L stainless steel, other suitable types of stainless steel, MP35N, or like materials. The connector 16 depicted in FIGS. 1, 2, 3, 4, and 5, eliminates the necessity for the conventionally used tubular crimping members and the attendant difficulties in establishing consistent and reliable crimped connections between the conductor wires of the lead and the various crimping members. Reliable electrical and mechanical connection between the conductor wires 42 and 44 and the connector 16 are established by welding. The use of welded connections in lieu of crimping tubes or slugs permits interim inspection and testing of the wire-to-connector connections and more rapid assembly.

Figure 6:
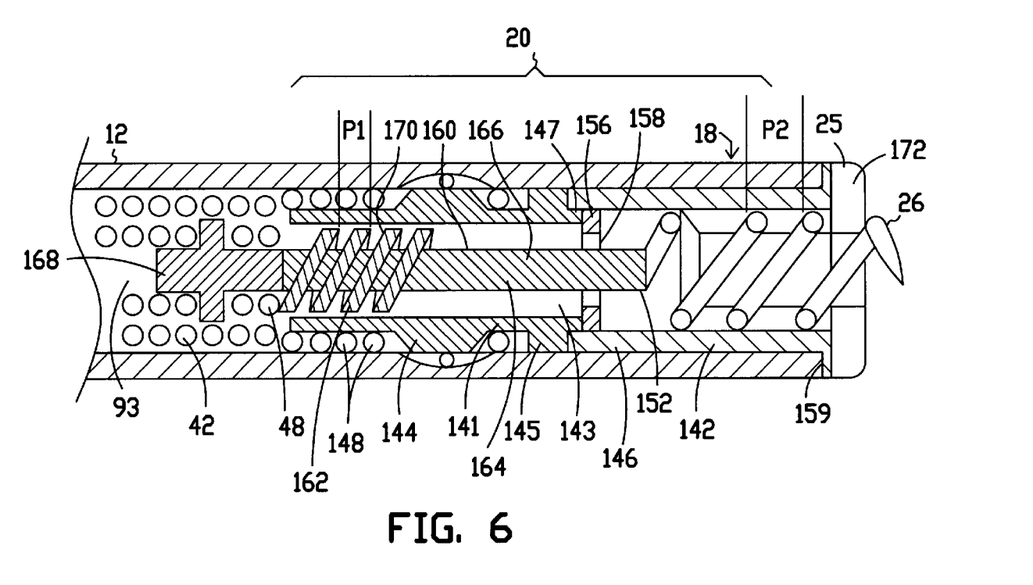
FIG. 6 is a cross-sectional view of FIG. 1 taken at section 6—6 in accordance with the present invention.

The detailed structure of the tip electrode 20 may be understood by referring now to FIG. 6, which is a cross-sectional view of FIG. 1 taken at section 6—6, and to FIG. 7, which is a detailed view of a portion of FIG. 6. The electrode 20 consists of a tubular shank 141 coupled to another tubular shank 142 and sharing a common, centrally disposed bore 143. The shank 141 includes a proximally disposed flange 144 and a distally positioned flange 145. The flange 145 abuts the proximal end 146 of the shank 142, and terminates short of the distal end of the shank 141 so that a distally facing annular shoulder 147 projects into the shank 142. Alternatively, the structure of the shanks 141 and 142 may be incorporated into a single piece.

The distal coils 148 of the conductor wire 42 are spiraled around the shank 141 so that at least one coil 148 is disposed between the flange 144 and the flange 145. This provides a mechanical capture of the coil or coils 148 to secure the wire 42 to the shank 141. The wire 42 is stripped distally to establish a conductive path to the shank 141. The wire 42 may also be secured by laser welding, other like welding techniques, or other suitable fastening methods. The main body of the shank 141 is provided with an outer diameter that is slightly larger than the inner diameter of the coils 148 of the wire 42, but smaller than that of the flanges 144 and 145. The distal coils 148 may be connected to the shank 141 by first urging the coils 148 over the main body of the shank 144 and then over the flange 144, and finally by welding, if desired.

The corkscrew 26 is shown in a partially extended position in FIG. 6. The corkscrew 26 is connected proximally to a threaded shaft 160 at 152 by laser welding or like techniques. The threaded shaft 160 is itself connected proximally to the torque coil 48 in a similar fashion. Rotation of the torque coil 48 causes the threaded shaft 160 to rotate. As the shaft 160 rotates, threads 162 on the shaft urge the corkscrew 26 to extend from or retract into the bore 143, depending on the direction of rotation and the type of threads, i.e., left or right handed. The threaded shaft 160 comprises a central core 164 with threads 162 on a central portion thereof. A distal end 166 of the core extends beyond the threads and passes through an annular washer 156, described below. the length of the distal end is sufficient to allow the corkscrew to be exposed outside the tip of the lead without the threads 162 encountering the washer 156. A proximal portion 168 of the central core may be provided proximal from the threads for securing the torque coil to the threaded shaft. The threads 162 on the threaded shaft engage female threads 170 on the inside of the bore 143.

For purposes of this invention, it is important that the pitch of the corkscrew be different from the pitch of the threads 162, more specifically, that the pitch of the corkscrew be greater than that of the threads 162. Because of this difference in pitch, the corkscrew will be exposed outside of the distal end of the lead at a slower rate than the rate at which the corkscrew will try to embed itself into an adjacent cardiac wall. The result will be that the distal end of the lead will be pulled into close contact with the cardiac wall, even if the corkscrew does not immediately pierce the wall as the corkscrew is exposed outside the distal tip of the lead. This results in an improved physical and electrical contact between the distal tip and the heart wall and makes it unlikely that the lead will need to be re-positioned.

It is also important that the difference between the two pitches should not be too great, or the corkscrew will not screw far enough into the heart wall before the distal tip is pulled into the wall far enough to prevent further rotation of the corkscrew. It is preferred, therefore, that the pitch of the corkscrew should be no more than twice the pitch of the threads 162.

As mentioned above, an annular washer 156 having a central aperture 158 is disposed inside the shank 142 and abutted against the annular shoulder 147 of the shank 141. The washer 156 is designed to provide some restriction to the influx of body fluids into the lumen 93 of the sleeve 12. The washer 156 may be composed of a variety of biocompatible flexible materials, such as, silicone, polyimide, or like materials. The aperture 158 is provided and sized to accommodate the torque coil 48.

The shanks 141 and 142 are inserted into the distal end 18 of the sleeve 12. The tip of the shank 142 is provided with an expanded diameter to establish a proximally facing annular shoulder 159 against which the distal end 18 is abutted. To secure the electrode 20 to the sleeve 12, a biocompatible adhesive is applied to the exterior of the shanks 141 and 142 prior to insertion into the distal end 18 of the sleeve 12. The adhesive may be a suitable medical grade adhesive, such as silicone based adhesive, a two-part adhesive, or similar adhesives. The electrical transmission capability of the tip 25 is enhanced by increasing the surface thereof exposed to myocardial tissue. In this regard, one or more slots 172 are provided in the face of the tip 25.

The shank 142 may be fabricated from a variety of biocompatible conducting materials, such as iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac stimulator lead having a proximal end and a distal end, said lead comprising:

a connector at said proximal end for connecting to a cardiac stimulator;

a tubular insulating sleeve having a first end coupled to the connector and a second end;

an electrode coupled to the second end and having a longitudinal bore;

a conductor wire disposed in the sleeve and coupled between the connector and the electrode for transmitting electric signals between the cardiac stimulator and the electrode, a corkscrew extendable through said distal end, said corkscrew having a selected first pitch, and a threaded shaft mounted within said distal end of said lead and connected to said corkscrew, said threaded shaft having threads with a selected second pitch, said first pitch being greater than said second pitch.

2. The cardiac stimulator lead according to claim 1 wherein said first pitch is no more than about two times greater than said second pitch.

3. The cardiac stimulator lead according to claim 1 wherein said threaded shaft comprises a first portion having threads thereon and a second, unthreaded portion, distal from said first portion, said second portion having a distal end and said corkscrew being affixed to said distal end.

4. The cardiac stimulator lead according to claim 3 further comprising a washer mounted transversely within said distal end of said lead, wherein said second portion passes through said washer.

5. The cardiac stimulator lead according to claim 4 further comprising a torque coil rotatably received within said sleeve, said torque coil having a distal end attached to said threaded shaft.

6. The cardiac stimulator lead according to claim 5 wherein said torque coil has a proximal end affixed to said connector and wherein said connector is rotatable with respect to said sleeve.

7. The cardiac stimulator lead according to claim 1 further comprising a torque coil rotatably received within said sleeve, said torque coil having a distal end attached to said threaded shaft.

8. The cardiac stimulator lead according to claim 7 wherein said torque coil has a proximal end affixed to said connector and wherein said connector is rotatable with respect to said sleeve.

9. The cardiac stimulator lead according to claim 1 wherein said distal tip comprises an electrode having a bore therethrough and wherein said corkscrew extends through said bore.

10. The cardiac stimulator lead according to claim 9 wherein said electrode has female threads within said bore, said female threads engaging said threaded shaft.

11. A lead having a proximal end and a distal end, said lead comprising:

a connector at said proximal end;

a tubular insulating sleeve having a first end and a second end, the first end coupled to the connector;

an electrode coupled to the second end and to the connector;

a corkscrew extendable through said distal end, said corkscrew having a selected first pitch, and a threaded shaft mounted within said distal end of said lead and connected to said corkscrew, said threaded shaft having threads with a selected second pitch, said first pitch being greater than said second pitch.

12. The lead according to claim 11, wherein the first pitch is substantially greater than the second pitch.

13. The lead according to claim 12, wherein said first pitch is no more than about two times greater than said second pitch.

14. The lead according to claim 11, wherein said threaded shaft includes a first portion and a second portion, the first portion having threads thereon, the second, unthreaded portion, distal from said first portion, said second portion having a distal end and said corkscrew being affixed to said distal end.

15. The lead according to claim 14, further comprising a washer mounted transversely within said distal end of said lead, wherein said second portion passes through said washer.

16. The lead according to claim 11, further comprising a torque coil rotatably received within said sleeve, said torque coil having a distal end attached to said threaded shaft.

17. The lead according to claim 16, wherein said torque coil has a proximal end affixed to said connector and wherein said connector is rotatable with respect to said sleeve.

18. The lead according to claim 11, wherein said electrode has a bore therethrough and wherein said corkscrew extends through said bore.

19. The lead according to claim 18, wherein said electrode has female threads within said bore, said female threadingly coupled with said threaded shaft.

20. The lead according to claim 11, further comprising a conductor wire disposed in the sleeve and coupled between the connector and the electrode.

21. The lead according to claim 20, wherein said electrode includes a shank having a first outer diameter, and the conductor wire has a second inner diameter, where the first outer diameter is greater than the second inner diameter.

22. The lead according to claim 20, wherein said electrode includes a shank having a proximal flange and a distal flange, and the conductor wire includes a coil disposed between the proximal flange and the distal flange.

23. A method comprising:

manipulating a lead extending from a proximal end to a distal end, the lead including an electrode;

rotating a handle at the proximal end at a first rate;

rotating a corkscrew at the distal end at a second rate, where the handle and the corkscrew are coupled with each other, and where the first rate is greater than the second rate; and advancing the corkscrew from the distal end of the lead.

24. The method as recited in claim 23, further comprising rotating a shaft having shaft threads, and engaging the shaft threads with a portion of the electrode, where the shaft is coupled with the corkscrew.

25. The method as recited in claim 24, wherein engaging the threads comprises engaging the shaft threads with electrode threads disposed within the electrode.

26. The method as recited in claim 23, wherein the electrode includes a shank having a proximal flange and a distal flange further comprising spiraling a wire around a shank so that at least one coil is disposed between the proximal flange and the distal flange.

27. A lead having a proximal end and a distal end, said lead comprising:

a connector at said proximal end;

a tubular insulating sleeve having a first end and a second end, the first end coupled to the connector;

an electrode coupled to the second end and to the connector;

a corkscrew extendable through said distal end, said corkscrew having a selected first pitch, and a threaded shaft mounted within said distal end of said lead and connected to said corkscrew, said threaded shaft having threads with a selected second pitch, said first pitch being greater than said second pitch, and said first pitch is no more than about two times greater than said second pitch.

28. A lead having a proximal end and a distal end, said lead comprising:
    a connector at said proximal end;
    a tubular insulating sleeve having a first end and a second end, the first end coupled to the connector;
    an electrode coupled to the second end and to the connector;
    a corkscrew extendable through said distal end, said corkscrew having a selected first pitch,
    a threaded shaft mounted within said distal end of said lead and connected to said corkscrew, said threaded shaft having threads with a selected second pitch, said first pitch being different than said second pitch; and
    a torque coil rotatably received within said sleeve, said torque coil having a distal end attached to said threaded shaft.

29. The lead according to claim 28, wherein said torque coil has a proximal end affixed to said connector and wherein said connector is rotatable with respect to said sleeve.

30. A lead having a proximal end and a distal end, said lead comprising:
    a connector at said proximal end;
    a tubular insulating sleeve having a first end and a second end, the first end coupled to the connector;
    an electrode coupled to the second end and to the connector;
    a corkscrew extendable through said distal end, said corkscrew having a selected first pitch;
    a threaded shaft mounted within said distal end of said lead and connected to said corkscrew, said threaded shaft having threads with a selected second pitch, said first pitch being different than said second pitch; and
    said electrode has a bore therethrough and wherein said corkscrew extends through said bore, and said electrode has female threads within said bore, said female threads threadingly coupled with said threaded shaft.

31. A lead having a proximal end and a distal end, said lead comprising:
    a connector at said proximal end;
    a tubular insulating sleeve having a first end and a second end, the first end coupled to the connector;
    an electrode coupled to the second end and to the connector;
    a corkscrew extendable through said distal end, said corkscrew having a selected first pitch;
    a threaded shaft mounted within said distal end of said lead and connected to said corkscrew, said threaded shaft having threads with a selected second pitch, said first pitch being different than said second pitch; and
    a conductor wire disposed in the sleeve and coupled between the connector and the electrode, and said electrode includes a shank having a first outer diameter, and the conductor wire has a second inner diameter, where the first outer diameter is greater than the second inner diameter.

32. A lead having a proximal end and a distal end, said lead comprising:
    a connector at said proximal end;
    a tubular insulating sleeve having a first end and a second end, the first end coupled to the connector;
    an electrode coupled to the second end and to the connector;
    a corkscrew extendable through said distal end, said corkscrew having a selected first pitch;
    a threaded shaft mounted within said distal end of said lead and connected to said corkscrew, said threaded shaft having threads with a selected second pitch, said first pitch being different than said second pitch; and
    a conductor wire disposed in the sleeve and coupled between the connector and the electrode, said electrode includes a shank having a proximal flange and a distal flange, and the conductor wire includes a coil disposed between the proximal flange and the distal flange.

33. A method comprising:
    manipulating a lead extending from a proximal end to a distal end, the lead including an electrode;
    rotating a handle at the proximal end at a first rate;
    rotating a corkscrew at the distal end at a second rate, where the handle and the corkscrew are coupled with each other, and where the first rate is different than the second rate;
    advancing the corkscrew from the distal end of the lead; and
    rotating a shaft having shaft threads, and engaging the shaft threads with a portion of the electrode, where the shaft is coupled with the corkscrew, engaging the threads comprises engaging the shaft threads with electrode threads disposed within the electrode.

34. A method comprising:
    manipulating a lead extending from a proximal end to a distal end, the lead including an electrode, where the electrode includes a shank having a proximal flange and a distal flange;
    spiraling a wire around a shank so that at least one coil is disposed between the proximal flange and the distal flange;
    rotating a handle at the proximal end at a first rate;
    rotating a corkscrew at the distal end at a second rate, where the handle and the corkscrew are coupled with each other, and where the first rate is different than the second rate; and
    advancing the corkscrew from the distal end of the lead.

* * * * *

UNITED STATES PATENT AND TRADEMARK OFFICE
CERTIFICATE OF CORRECTION

PATENT NO. : 6,269,272 B1
DATED : July 31, 2001
INVENTOR(S) : Fischer, Sr.

It is certified that error appears in the above-identified patent and that said Letters Patent is hereby corrected as shown below:

<u>Column 5,</u>
Lines 38 and 41, delete "stiffiness" and insert -- stiffness --, therefor.

Signed and Sealed this

Ninth Day of April, 2002

Attest:

Attesting Officer

JAMES E. ROGAN
*Director of the United States Patent and Trademark Office*